US009838610B2

United States Patent
Sakai et al.

(10) Patent No.: US 9,838,610 B2
(45) Date of Patent: Dec. 5, 2017

(54) IMAGING SYSTEM (71) Applicant: OLYMPUS CORPORATION, Tokyo (JP)

(72) Inventors: Aiko Sakai, Kodaira (JP); Satoshi Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/618,505

(22) Filed: Jun. 9, 2017

(65) Prior Publication Data

US 2017/0280037 A1 Sep. 28, 2017

Related U.S. Application Data (63) Continuation of application No. PCT/JP2016/078063, filed on Sep. 23, 2016.

(30) Foreign Application Priority Data

Oct. 7, 2015 (JP) ................................ 2015-199370

(51) Int. Cl.
*A61B 1/00* (2006.01)
*H04N 5/235* (2006.01)
(Continued)

(52) U.S. Cl.
CPC ....... *H04N 5/2353* (2013.01); *A61B 1/00006* (2013.01); *A61B 1/00009* (2013.01);
(Continued)

(58) Field of Classification Search
CPC ......... H04N 2005/2255; H04N 5/2354; H04N 5/2256; A61B 1/05; A61B 1/042
See application file for complete search history.

(56) References Cited

U.S. PATENT DOCUMENTS 5,784,098 A * 7/1998 Shoji ..................... G01B 11/25
348/139
5,840,017 A * 11/1998 Furusawa .......... A61B 1/00186
600/109
(Continued)

FOREIGN PATENT DOCUMENTS

JP 2005-204741 A 8/2005
JP 2010-005001 A 1/2010
(Continued)

OTHER PUBLICATIONS

International Search Report dated Nov. 8, 2016 issued in PCT/JP2016/078063.
(Continued)

*Primary Examiner* — Sath V Perungavoor
*Assistant Examiner* — Howard D Brown, Jr.
(74) *Attorney, Agent, or Firm* — Scully, Scott, Murphy & Presser, P.C.

(57) ABSTRACT

An imaging system includes: an imaging device including an image sensor provided with an electronic shutter function, the imaging device being configured to capture a subject; a light source configured to emit illumination light for illuminating the subject; an identification unit configured to identify which one of a first light source and a second light source configured to emit light having a wavelength bandwidth different from a wavelength bandwidth of the first light source is employed as the light source used for observation; an electronic shutter controller configured to control the electronic shutter function of the image sensor based on a control pattern according to the classification of the light source identified by the identification unit; and an electronic shutter control pattern setting unit configured to set a control pattern of the electronic shutter function in accordance with
(Continued)

the classification of the light source identified by the identification unit.

8 Claims, 7 Drawing Sheets (51) Int. Cl.
*H04N 5/225* (2006.01)
*A61B 1/045* (2006.01)
*A61B 1/06* (2006.01)
*A61B 5/00* (2006.01)
*A61B 1/07* (2006.01)
*G02B 23/24* (2006.01)

(52) U.S. Cl.
CPC ............ *A61B 1/045* (2013.01); *A61B 1/0638* (2013.01); *A61B 1/0669* (2013.01); *A61B 1/07* (2013.01); *A61B 5/0086* (2013.01); *H04N 5/2256* (2013.01); *H04N 2005/2255* (2013.01)

(56) References Cited

U.S. PATENT DOCUMENTS

| 6,635,011 | B1* | 10/2003 | Ozawa | A61B 1/00096 |
| | | | | 348/E5.029 |
| 2008/0287742 | A1* | 11/2008 | St. George | A61B 1/00036 |
| | | | | 600/160 |
| 2014/0364690 | A1* | 12/2014 | Seto | G02B 23/2461 |
| | | | | 600/109 |

FOREIGN PATENT DOCUMENTS

| JP | 2011-206336 A | 10/2011 |
| JP | 2012-010282 A | 1/2012 |
| JP | 2012-183240 A | 9/2012 |
| WO | WO 2013/146311 A1 | 10/2013 |

OTHER PUBLICATIONS

Japanese Office Action dated Feb. 21, 2017 issued in JP 2016-573640.

* cited by examiner

| INTERNAL LIGHT SOURCE | EXTERNAL LIGHT SOURCE |
|---|---|
| FIX ELECTRONIC SHUTTER TO TURNING ON | SELECTIVELY SWITCH ELECTRONIC SHUTTER BETWEEN TURNING ON AND TURNING OFF |

| FIRST LIGHT SOURCE | SECOND LIGHT SOURCE T1-1 |
|---|---|
| FIX ELECTRONIC SHUTTER TO TURNING ON | SELECTIVELY SWITCH ELECTRONIC SHUTTER BETWEEN TURNING ON AND TURNING OFF |

FIG.7

| IMAGE SENSOR \ LIGHT SOURCE | INTERNAL LIGHT SOURCE | EXTERNAL LIGHT SOURCE |
|---|---|---|
| HIGH-SENSITIVITY IMAGE SENSOR | FIX ELECTRONIC SHUTTER TO TURNING ON | SELECTIVELY SWITCH ELECTRONIC SHUTTER BETWEEN TURNING ON AND TURNING OFF |
| LOW-SENSITIVITY IMAGE SENSOR | TURN OFF ELECTRONIC SHUTTER | NO CONNECTION IS SET |

| ILLUMINATION LIGHT / IMAGE SENSOR | WHITE LIGHT | SPECIAL LIGHT | T2-1 |
|---|---|---|---|
| HIGH-SENSITIVITY IMAGE SENSOR | FIX ELECTRONIC SHUTTER TO TURNING ON | SELECTIVELY SWITCH ELECTRONIC SHUTTER BETWEEN TURNING ON AND TURNING OFF | |
| LOW-SENSITIVITY IMAGE SENSOR | TURN OFF ELECTRONIC SHUTTER | TURN OFF ELECTRONIC SHUTTER | |

FIG.10

| HIGH-SENSITIVITY IMAGE SENSOR | LOW-SENSITIVITY IMAGE SENSOR | T2-2 |
|---|---|---|
| FIX ELECTRONIC SHUTTER TO TURNING ON | SELECTIVELY SWITCH ELECTRONIC SHUTTER BETWEEN TURNING ON AND TURNING OFF | |

IMAGING SYSTEM

CROSS-REFERENCE TO RELATED APPLICATIONS

This application is a continuation of PCT international application Ser. No. PCT/JP2016/078063 filed on Sep. 23, 2016 which designates the United States, incorporated herein by reference, and which claims the benefit of priority from Japanese Patent Applications No. 2015-199370, filed on Oct. 7, 2015, incorporated herein by reference.

BACKGROUND

The present invention relates to an imaging system.

An endoscope system has been used in a medical field in the past to observe the inside of a subject. Typically, the endoscope captures an in-vivo image by inserting an insertion portion having an elongated shape into the subject such as a patient to exit illumination light supplied by a light source device through a distal end of this insertion portion and then receive reflected light of this illumination light using an image sensor. A processing device (processor) of the endoscope system applies predetermined image processing to the in-vivo image captured by the image sensor of the endoscope. Thereafter, this in-vivo image is presented on a display of the endoscope system. A user such as a medical doctor observes an organ of the subject based on the in-vivo image presented on the display.

Illumination light is switched during the observation using the endoscope by choosing which one of an internal light source and an external light source to use depending on a purpose of observation or an observed region. In order to enhance image quality of an in-vivo image, an endoscope system configured to adjust a color tone by changing a white balance to be used in the image processing to a white balance suitable for the switched illumination light has been suggested in recent years (for example, refer to JP 2012-183240 A).

There is a need for an imaging system capable of obtaining an image with proper brightness regardless of classifications of light sources.

SUMMARY

An imaging system according to one aspect of the present invention includes: an imaging device including an image sensor provided with an electronic shutter function, the imaging device being configured to capture a subject; a light source configured to emit illumination light for illuminating the subject; an identification unit configured to identify which one of a first light source and a second light source configured to emit light having a wavelength bandwidth different from a wavelength bandwidth of the first light source is employed as the light source used for observation; an electronic shutter controller configured to control the electronic shutter function of the image sensor based on a control pattern according to the classification of the light source identified by the identification unit; and an electronic shutter control pattern setting unit configured to set a control pattern of the electronic shutter function in accordance with the classification of the light source identified by the identification unit, and the electronic shutter control pattern setting unit sets a control pattern to use the electronic shutter function when the identification unit identifies that the light source is the first light source and sets a control pattern to selectively make switching between using the electronic shutter function and not using the electronic shutter function when the identification unit identifies that the light source is the second light source.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

In the following explanation, an endoscope system for medical use will be described as modes for carrying out the invention (hereinafter, referred to as "embodiments"). The embodiments are not construed to limit the invention. Additionally, in the descriptions of the drawings, similar portions are given similar reference numerals.

First Embodiment

Figure 1:
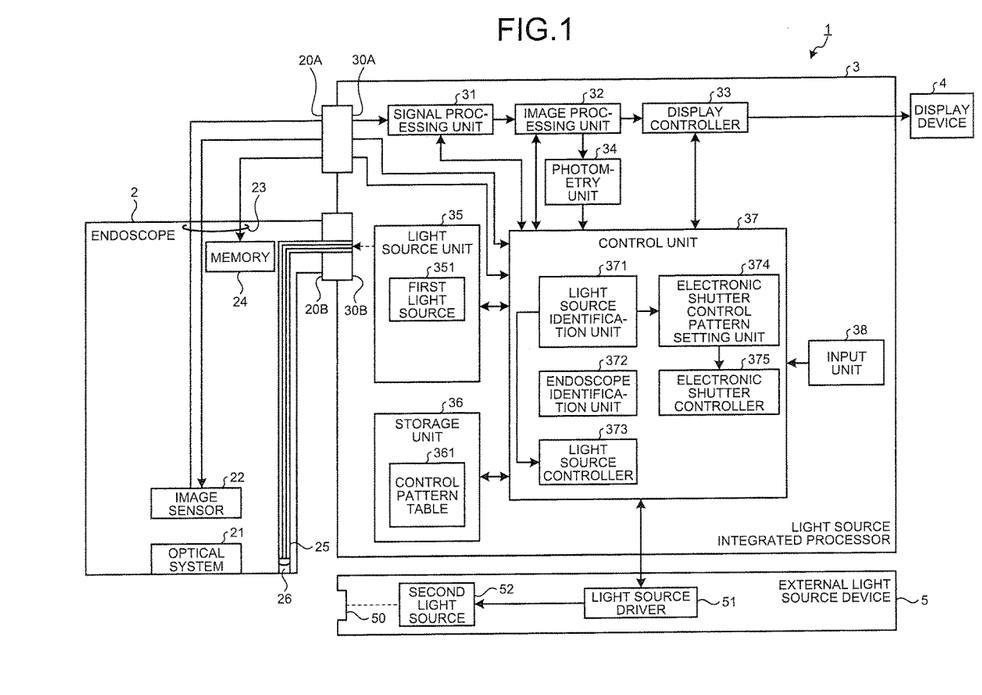
FIG. 1 is a schematic diagram illustrating an overview configuration of an endoscope system according to a first embodiment of the invention.

FIG. 1 is a schematic diagram illustrating an overview configuration of an endoscope system according to a first embodiment of the invention. As illustrated in FIG. 1, the endoscope system 1 according to the first embodiment includes an endoscope 2 (imaging device) with flexibility to be put into a subject, a light source integrated processor 3 (control device) that carries out predetermined image processing on an imaging signal sent from the endoscope 2 electrically connected thereto via connectors 20A and 30A, a display device 4 that displays an in-vivo image corresponding to an image signal to which the light source integrated processor 3 has applied the image processing, and an external light source device 5 having a second light source configured to supply infrared light to the endoscope 2 optically connected thereto. The light source integrated processor 3 is configured in such a manner that a connector 20B of the endoscope 2 is optically connected thereto via a connector 30B so as to be freely attached and detached. While the connector 20B of the endoscope 2 is mounted to the connector 30B of the light source integrated processor 3, light supplied from the light source integrated processor 3 emits through a distal end of the endoscope 2 as illumination light. While the connector 20B of the endoscope 2 is mounted to a connector 50 of the external light source device 5, infrared light supplied from the external light source device 5 emits through the distal end of the endoscope 2 as illumination light.

The endoscope 2 has an insertion portion to be inserted into the subject. An image sensor 22 provided at a distal end portion of the insertion portion generates image data of the inside of the subject by capturing the interior of the body of the subject. The endoscope 2 includes the connectors 20A and 20B provided at a proximal end portion, an optical system 21, the image sensor 22, and an illumination lens 26 provided at a distal end portion, an electric cable 23 of which a distal end is connected to the image sensor 22 and a memory 24 and of which a proximal end extends to the connector 20A, the memory 24, and an illumination fiber (light guide cable) 25 extending from the distal end portion of the endoscope 2 to the connector 20B at a proximal end thereof. The endoscope 2 also has an operation switch unit (not illustrated) on which various operation switches are provided. The illumination lens 26 is provided on a distal end side of the light guide cable 25 such that an object is irradiated with light emitting from the light source integrated processor 3 or the external light source device 5 through the illumination lens 26.

The optical system 21 is constituted using one lens or a plurality of lenses and provided at a former stage of the image sensor 22 to form an image of incident light from the object. The optical system 21 has an optical zoom function to vary an angle of view and a focus function to vary a focal point.

The image sensor 22 captures an optical image formed by the optical system 21 to generate the imaging signal. The image sensor 22 includes an electronic shutter function such that an exposure period is altered under the control of the light source integrated processor 3. The image sensor 22 is, for example, a CMOS image sensor or a CCD image sensor, in which a plurality of pixels that receive light from the object irradiated with light and then photoelectrically convert the received light to generate the image data is arranged on a light-receiving surface in a matrix form.

The memory 24 records identification information indicating a classification, a generation, and a model number of the endoscope 2, a classification of the image sensor 22, and so on. In addition, the memory 24 may also record various parameters used in image processing for the imaging signal captured by the image sensor 22, such as a parameter for white balance (WB) adjustment. Various items of information recorded by the memory 24 are output to a control unit 37 of the light source integrated processor 3 via the electric cable 23 and the connectors 20A and 30A through communication processing with the light source integrated processor 3 while the endoscope 2 is mounted on the light source integrated processor 3.

The illumination lens 26 is positioned at a distal end of the light guide cable 25 extending from the connector 20B. While the endoscope 2 is optically mounted on the light source integrated processor 3, the object is irradiated with light emitting from a first light source 351 of a light source unit 35 (described later) through the illumination lens 26 located at a distal end of the endoscope 2 by way of the light guide cable 25. While the endoscope 2 is optically mounted on the external light source device 5, the object is irradiated with infrared light emitting from a second light source 52 (described later) through the illumination lens 26 located at the distal end of the endoscope 2 by way of the light guide cable 25.

The endoscope 2 is mounted on the light source integrated processor 3 so as to be freely attached and detached, whereby the light source integrated processor 3 applies the predetermined image processing to the imaging signal sent from the mounted endoscope 2 and then generates the in-vivo image. The light source integrated processor 3 outputs the generated in-vivo image to the display device 4 to display thereon.

The light source integrated processor 3 includes a signal processing unit 31, an image processing unit 32 (imaging signal processing unit), a display controller 33, a photometry unit 34 (photometry unit), the light source unit 35, a storage unit 36, the control unit 37, and an input unit 38.

The signal processing unit 31 has an analog processing unit that carries out noise removal processing and clamp processing on the imaging signal (analog) output from the image sensor 22 and an A/D converter that carries out A/D conversion processing, to output the imaging signal (digital). In addition, a configuration with the signal processing unit 31 provided in the endoscope 2 is also considered.

The image processing unit 32 applies the predetermined image processing to the imaging signal generated by the image sensor 22 of the endoscope 2. The image processing unit 32 carries out, for example, optical black (OB) subtraction processing, demosaicing processing, white balance (WB) adjustment processing, electronic zoom processing, edge emphasis processing, mask processing, and on-screen display (OSD) processing on the imaging signal (digital) output from the signal processing unit 31 and thereafter, outputs an image signal generated through such processing.

The display controller 33 converts the image signal generated by the image processing unit 32 to a format allowing the display device 4 to display and output and then causes the display device 4 to display. The display controller 33 includes a converter from a digital signal to an analog signal (DAC) and an encoder to convert the image signal input from the image processing unit 32 to, for example, an analog signal from a digital signal and then alter the image data converted to the analog signal to a format such as a high-vision mode to output to the display device 4.

The photometry unit 34 measures the brightness of the object to be captured by the image sensor 22 depending on the imaging signal from the image sensor 22 to generate a photometric value. For example, the photometry unit 34 acquires the imaging signal for a sample from the image processing unit 32 and detects the photometric value corresponding to each of pixels to output the detected photometric value to the control unit 37.

The light source unit 35 is an internal light source provided within the same casing device as the image processing unit 32 configured to process the imaging signal generated by the image sensor 22. The light source unit 35 has the first light source 351 to supply the illumination light to the endoscope 2 optically connected thereto via the connector 30B. The object is irradiated with light emitting from the light source unit 35 through the illumination lens 26 located at the distal end of the endoscope 2 by way of the light guide cable 25 of the endoscope 2 optically connected to the connector 30B.

The first light source 351 is constituted by, for example, a white LED. In addition, the first light source 351 may be configured to use a plurality of LEDs that emit light having different wavelength bandwidths from one another (e.g., a red LED, a green LED, and a blue LED) and multiplex light emitting from the respective LEDs such that a desired color tone of the illumination light is obtained. Meanwhile, the light source unit 35 may adopt a configuration using sequential lighting in which light having different color components is emitted in time series. Alternatively, the first light source 351 may be a laser light source. Alternatively, the light source unit 35 may have a configuration including a light source such as a xenon lamp or a halogen lamp and a light source control component that controls an optical filter, a diaphragm, and respective members of the light source unit 35. The light source unit 35 may be configured to further include an optical filter that only allows blue light having a blue wavelength component converted into a narrow bandwidth and a green wavelength component to pass therethrough such that so-called narrow band imaging (NBI) light is additionally emitted as special light.

Figure 2:
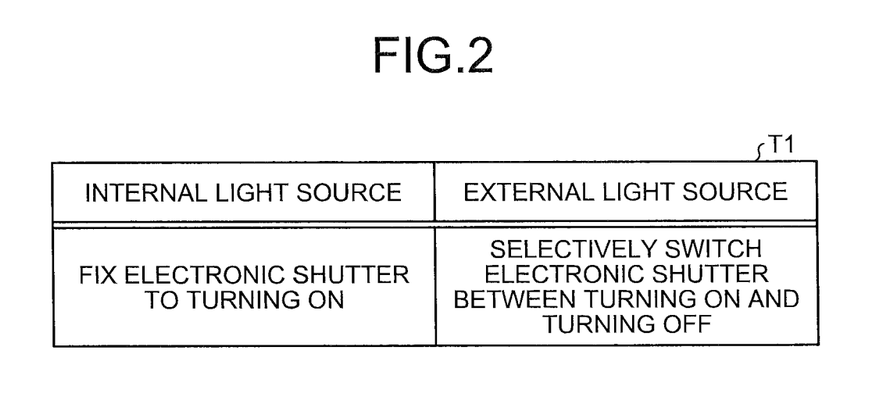
FIG. 2 is a diagram illustrating an exemplary control pattern table stored in a storage unit illustrated in FIG. 1.

The storage unit 36 is implemented using, for example, a volatile memory or a non-volatile memory and stores various programs for causing the light source integrated processor 3 to work. The storage unit 36 temporarily stores information obtained during processing by the light source integrated processor 3. The storage unit 36 stores a control pattern table 361 indicating a control pattern of the electronic shutter function of the image sensor 22. FIG. 2 is a diagram illustrating an example of the control pattern table 361 stored in the storage unit 36. As illustrated in FIG. 2, the storage unit 36 stores a table T1 as the control pattern table 361, in which each of classifications of light sources is associated with a control pattern of the electronic shutter function of the image sensor 22. The table T1 in FIG. 2 illustrates the light source unit 35 serving as an internal light source and the external light source device 5 serving as an external light source as classifications of light sources. In table T1, a control pattern to always turn on the electronic shutter function is associated with the internal light source, whereas a control pattern to selectively switch the electronic shutter function between turning on and turning off is associated with the external light source. The storage unit 36 stores various items of information such as the image signal and the identification information output from the endoscope 2. The storage unit 36 may be constituted using a memory card or the like mounted from the outside of the light source integrated processor 3.

The control unit 37 is implemented using, for example, a CPU. The control unit 37, for example, transfers instruction information and data to respective components of the light source integrated processor 3, thereby controlling processing actions of respective constituent members of the light source integrated processor 3. While the endoscope 2 is mounted on the light source integrated processor 3, the control unit 37 is connected to the image sensor 22 of the endoscope 2 via the electric cable 23, thereby controlling these units. The control unit 37 makes connection to the memory 24 of the endoscope 2 via the electric cable 23 to, for example, retrieve information recorded in the memory 24. The control unit 37 has a light source identification unit 371, an endoscope identification unit 372, a light source controller 373, an electronic shutter control pattern setting unit 374, and an electronic shutter controller 375.

The light source identification unit 371 identifies which one of the internal first light source 351 and the second light source 52 of the external light source device 5 is employed as a light source used for observation, based on the instruction information and so on input from the input unit 38 described later. Depending on whether the light guide cable 25 of the endoscope 2 is connected to a light-emitting terminal of the internal first light source 351 or a light-emitting terminal of the external light source device 5, the light source identification unit 371 identifies which one of the first light source 351 and the second light source 52 of the external light source device 5 is employed as the light source used for observation. When the external light source device 5 is used for observation, the light source identification unit 371 may carry out communication processing with the external light source device 5 to identify the classification of a light source used as the external light source.

The endoscope identification unit 372 retrieves the identification information from the memory 24 of the endoscope 2 mounted on the light source integrated processor 3 to identify the classification of the endoscope 2. The endoscope identification unit 372 identifies the classification of the image sensor 22 of the endoscope 2 electrically mounted on the light source integrated processor 3.

The light source controller 373 sets an amount of light emission (including intensity and a time) based on a photometric value detected by the photometry unit 34 and controls in such a manner that the first light source 351 or the second light source 52 emits light by the set amount of light emission.

The electronic shutter control pattern setting unit 374 sets the control pattern of the electronic shutter function of the image sensor 22 in accordance with the classification of the light source identified by the light source identification unit 371. The electronic shutter control pattern setting unit 374 retrieves, from the control pattern table 361 of the storage unit 36, a control pattern of the electronic shutter function according to the classification of the light source identified by the light source identification unit 371 and then sets the retrieved control pattern as the control pattern of the electronic shutter function of the image sensor 22. The electronic shutter control pattern setting unit 374 sets the control pattern of the electronic shutter function from among a control pattern to always turn off the electronic shutter function, a control pattern to always turn on the electronic shutter function, and a control pattern to selectively switch the electronic shutter function between turning on and turning off. The control pattern to always turn off the electronic shutter function controls such that an exposure time of the image sensor 22 is not limited. The control pattern to always turn on the electronic shutter function controls such that the exposure time of the image sensor 22 is altered based on the photometric value according to the photometry unit 34. The control pattern to selectively switch the electronic shutter function between turning on and turning off controls such that control to alter the exposure time of the image sensor 22 and control not to limit the exposure time of the image sensor 22 can be selected based on the photometric value according to the photometry unit 34.

The electronic shutter controller 375 controls the electronic shutter function of the image sensor 22 based on the control pattern set by the electronic shutter control pattern setting unit 374. The electronic shutter controller 375 controls the electronic shutter function based on the control pattern set by the electronic shutter control pattern setting unit 374 and the photometric value by the photometry unit 34. When the electronic shutter control pattern setting unit 374 sets the control pattern to always turn on the electronic shutter function, the electronic shutter controller 375 alters the exposure time of the image sensor 22 based on the photometric value according to the photometry unit 34. In different words, the electronic shutter controller 375 sets an amount of exposure of the image sensor 22 based on the photometric value according to the photometry unit 34 and controls the image sensor 22 such that the image sensor 22 allows exposure for an exposure time according to the set amount of exposure. When the electronic shutter control pattern setting unit 374 sets the control pattern to always turn off the electronic shutter function, the electronic shutter controller 375 does not limit the exposure time of the image sensor 22. When the electronic shutter control pattern setting unit 374 sets the control pattern to selectively switch the electronic shutter function between turning on and turning off, the electronic shutter controller 375 controls the electronic shutter function of the image sensor 22 while making selection between control to alter the exposure time of the image sensor 22 and control not to limit the exposure time of the image sensor 22 based on the photometric value according to the photometry unit 34.

The input unit 38 accepts input of various types of instruction information and inputs the instruction information to the light source integrated processor 3. The input unit 38 accepts input of light source switching instruction information for switching the light source to emit the illumination light used for observation to one of the first light source 351 and the second light source 52. The input unit 38 inputs the various types of instruction information that have been accepted to the control unit 37 of the light source integrated processor 3. The input unit 38 accepts input of patient data (e.g., an ID, a date of birth, and a name) regarding a particular patient serving as the subject and data such as examination details. The input unit 38 may be an operation device such as a button or a touch panel provided on a front panel of the light source integrated processor 3. The input unit 38 may be implemented using an operation device such as a mouse and a keyboard connected to a main body section of the light source integrated processor 3. The input unit 38 may be a switch or the like provided on a grip section of the endoscope 2. The input unit 38 may be of a type where the instruction information is input thereto through remote operation from a portable terminal device such as a tablet type terminal device.

The display device 4 is constituted using a display apparatus or the like employing a liquid crystal or organic EL. The display device 4 displays various items of information including a display image output from the light source integrated processor 3.

The external light source device 5 has a light source driver 51 and the second light source 52 to supply the illumination light to the endoscope 2 optically connected thereto via the connector 50, under the control of the control unit 37. The external light source device 5 supplies the infrared light. Note that the external light source device 5 is not limited to a type for supplying the infrared light but only required to supply light having a wavelength bandwidth different from that of the light source unit 35 within the light source integrated processor 3.

The light source driver 51 supplies predetermined electric power to the second light source 52 under the control of the light source controller 373. The second light source 52 is constituted using, for example, a light source configured to emit the infrared light and an optical system such as a condenser lens. The object is irradiated with the infrared light emitting from the second light source 52 through the illumination lens 26 located at the distal end of the endoscope 2 by way of the light guide cable 25 of the endoscope 2 optically connected to the connector 50. Note that the image sensor 22 is arranged in the vicinity of the illumination lens 26.

Figure 3:
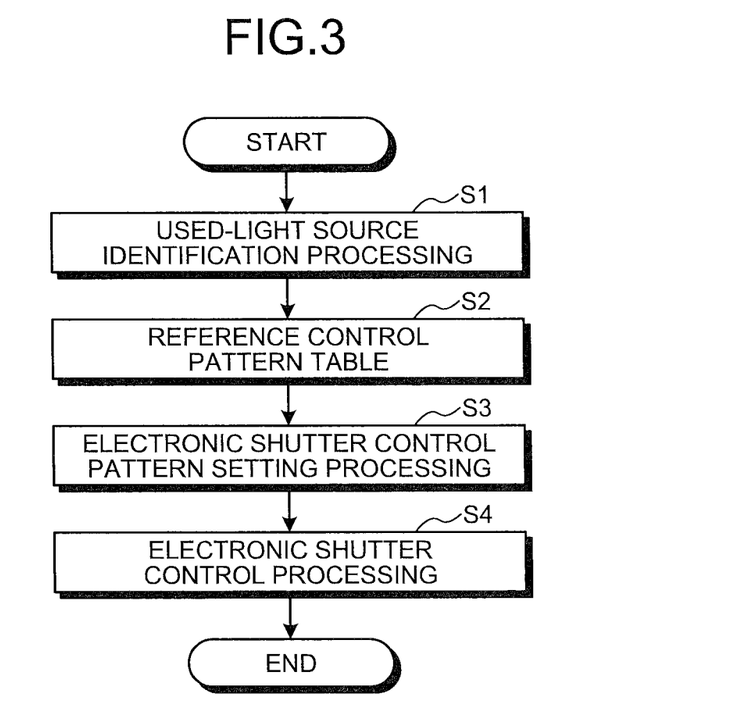
FIG. 3 is a flowchart illustrating processing procedures of electronic shutter function control processing for an image sensor of an endoscope by a light source integrated processor illustrated in FIG. 1.

FIG. 3 is a flowchart illustrating processing procedures of electronic shutter function control processing for the image sensor 22 of the endoscope 2 by the light source integrated processor 3. As illustrated in FIG. 3, the light source integrated processor 3 carries out used-light source identification processing to identify the classification of the light source used for observation, based on the instruction information and so on input from the input unit 38 (step S1). The electronic shutter control pattern setting unit 374 references the control pattern table 361 in the storage unit 36 (step S2) to retrieve, from the control pattern table 361, the control pattern of the electronic shutter function according to the classification of the light source identified by the light source identification unit 371 and then carries out electronic shutter control pattern setting processing to set the retrieved control pattern as the control pattern of the electronic shutter function of the image sensor 22 (step S3). The electronic shutter controller 375 carries out electronic shutter control processing to control the electronic shutter function of the image sensor 22 based on the control pattern set by the electronic shutter control pattern setting unit 374 (step S4).

When the light source identification unit 371 identifies, during the used-light source identification processing (step S1), that the light source used for observation is the internal light source (first light source 351), the electronic shutter control pattern setting unit 374 references the table T1 (step S2) and then sets a control pattern to fix the electronic shutter function to always turning on (step S3). Accordingly, when the white light from the first light source 351 is used for observation, the electronic shutter controller 375 controls the image sensor 22 using the control pattern to fix the electronic shutter function to always turning on and thus, the amount of exposure in the image sensor 22 is adjusted as appropriate in accordance with the brightness of an image.

On the other hand, when the light source identification unit 371 identifies, during the used-light source identification processing (step S1), that the light source used for observation is the external light source (second light source 52), the electronic shutter control pattern setting unit 374 references the table T1 (step S2) and then sets a control pattern to selectively switch the electronic shutter function between turning on and turning off (step S3). Accordingly, when the infrared light from the second light source 52 is used for observation, the electronic shutter controller 375 selectively switches the electronic shutter function between turning on and off and thus, it is made possible to carry out control not to limit the exposure time through an electronic shutter such that sufficient brightness is ensured even with darker infrared light.

As described thus far, according to the first embodiment, the control pattern of the electronic shutter function of the image sensor 22 is set in accordance with the classification of the light source used for observation. Consequently, optimum control of the electronic shutter function provided in the image sensor 22 can be automatically carried out regardless of classifications of light sources, whereby an image with proper brightness can be obtained.

Modified Example of First Embodiment

Figure 4:
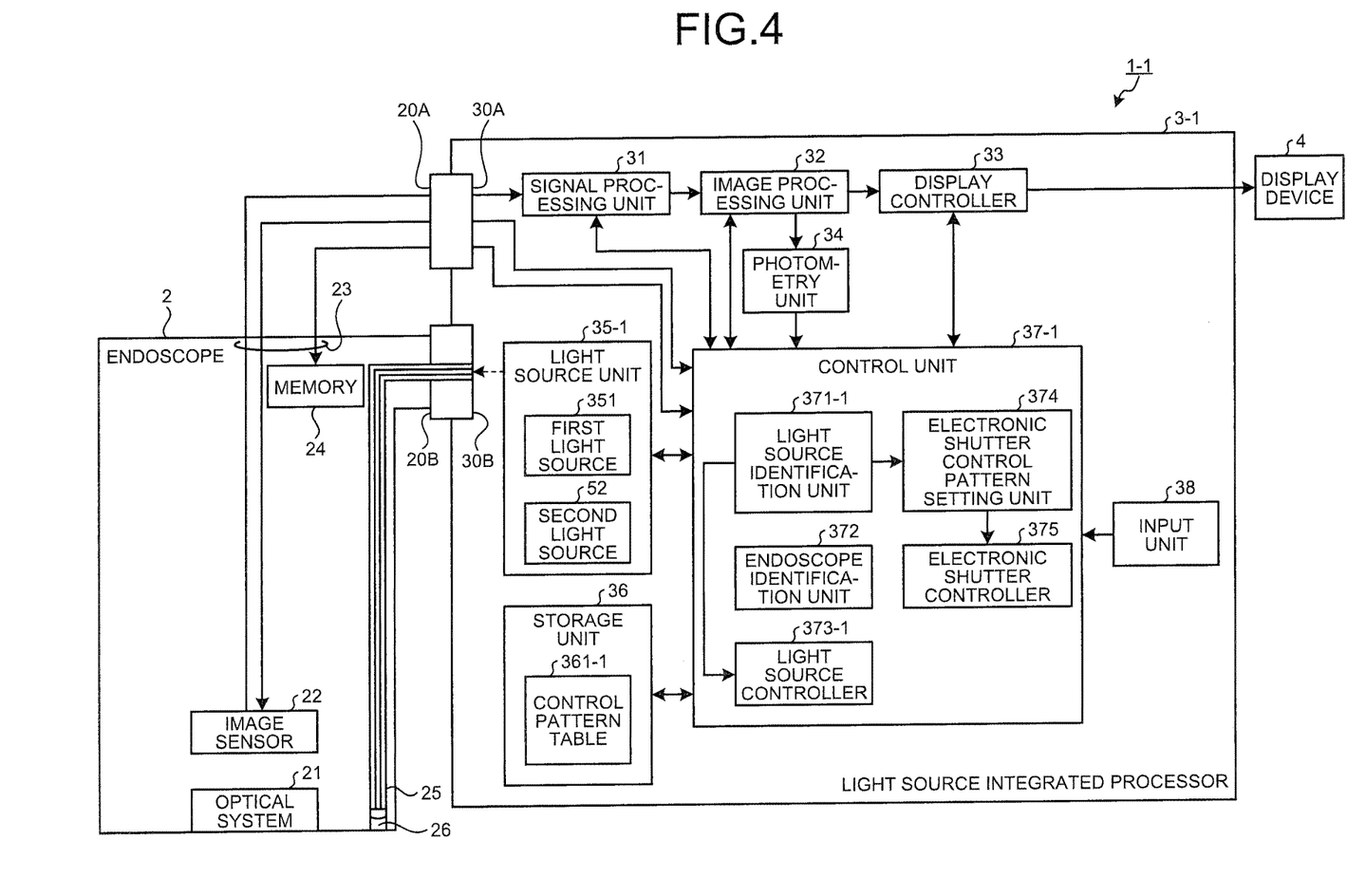
FIG. 4 is a schematic diagram illustrating an overview configuration of an endoscope system according to a modified example of the first embodiment.

FIG. 4 is a schematic diagram illustrating an overview configuration of an endoscope system according to a modified example of the first embodiment of the invention.

As illustrated in FIG. 4, the endoscope system 1-1 according to the modified example of the first embodiment is configured in such a manner that a light source unit 35-1 of a light source integrated processor 3-1 has both of a first light source 351 and a second light source 52. A light source identification unit 371-1 of a control unit 37-1 identifies which one of the first light source 351 and the second light source 52 is employed as a light source used for observation, based on the instruction information and so on input from an input unit 38. A light source controller 373-1 controls the light source used for observation among the first light source 351 and the second light source 52.

Figure 5:
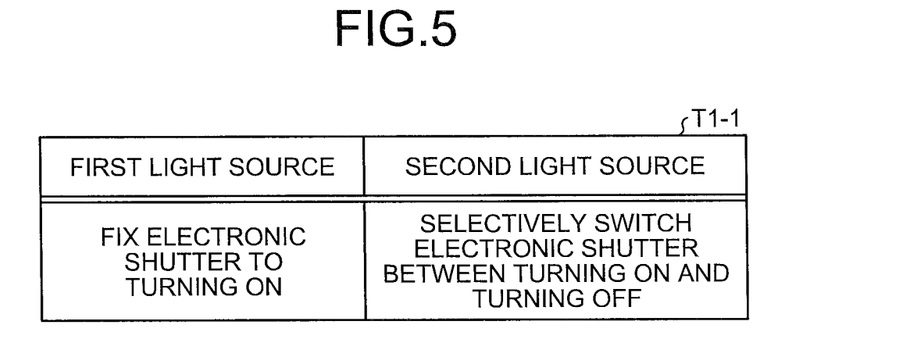
FIG. 5 is a diagram illustrating an exemplary control pattern table stored in a storage unit illustrated in FIG. 4.

A storage unit 36 stores a control pattern table 361-1. FIG. 5 is a diagram illustrating an example of the control pattern table 361-1. As illustrated in FIG. 5, the storage unit 36 stores a table T1-1 as the control pattern table 361-1, in which a control pattern to always turn on the electronic shutter function is associated with the first light source 351 and a control pattern to selectively switch the electronic shutter function between turning on and turning off is associated with the second light source 52.

Accordingly, when the light source identification unit 371-1 identifies, during the used-light source identification processing (step S1 in FIG. 3), that the light source used for observation is the first light source 351, the electronic shutter control pattern setting unit 374 references the table T1-1 (step S2) and then sets a control pattern to fix the electronic shutter function to always turning on (step S3). On the other hand, when the light source identification unit 371-1 identifies, during the used-light source identification processing (step S1), that the light source used for observation is the second light source 52, the electronic shutter control pattern setting unit 374 references the table T1-1 (step S2) and then sets a control pattern to selectively switch the electronic shutter function between turning on and turning off (step S3).

As in this modified example of the first embodiment, also when the light source integrated processor 3-1 has therein both of the first light source 351 and the second light source 52, an effect similar to that of the first embodiment can be achieved as long as the control pattern of the electronic shutter function of the image sensor 22 is set in accordance with the classification of the light source used for observation.

Second Embodiment

Figure 6:
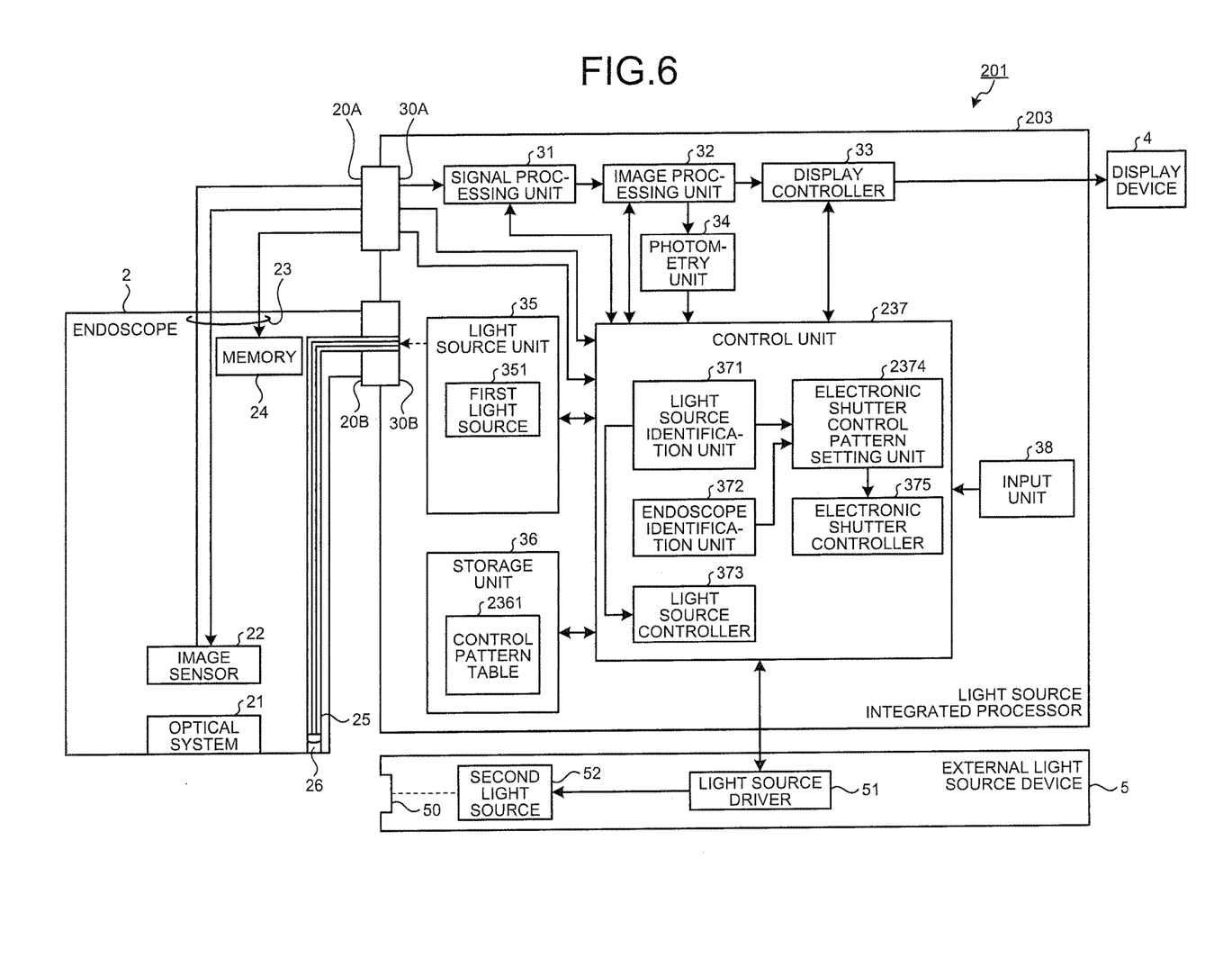
FIG. 6 is a schematic diagram illustrating an overview configuration of an endoscope system according to a second embodiment.

FIG. 6 is a schematic diagram illustrating an overview configuration of an endoscope system according to a second embodiment. As illustrated in FIG. 6, the endoscope system 201 according to the second embodiment is configured in such a manner that a light source integrated processor 203 includes a control unit 237 having an electronic shutter control pattern setting unit 2374.

The electronic shutter control pattern setting unit 2374 sets the control pattern of the electronic shutter function in accordance with the classification of the light source identified by a light source identification unit 371 and the classification of an image sensor 22 identified by an endoscope identification unit 372. An electronic shutter controller 375 controls the electronic shutter function of the image sensor 22 based on the control pattern set by the electronic shutter control pattern setting unit 2374. In different words, the electronic shutter controller 375 controls the electronic shutter function of the image sensor 22 based on the control pattern according to the classification of the light source identified by the light source identification unit 371 and the classification of the image sensor 22 identified by the endoscope identification unit 372.

Figure 7:
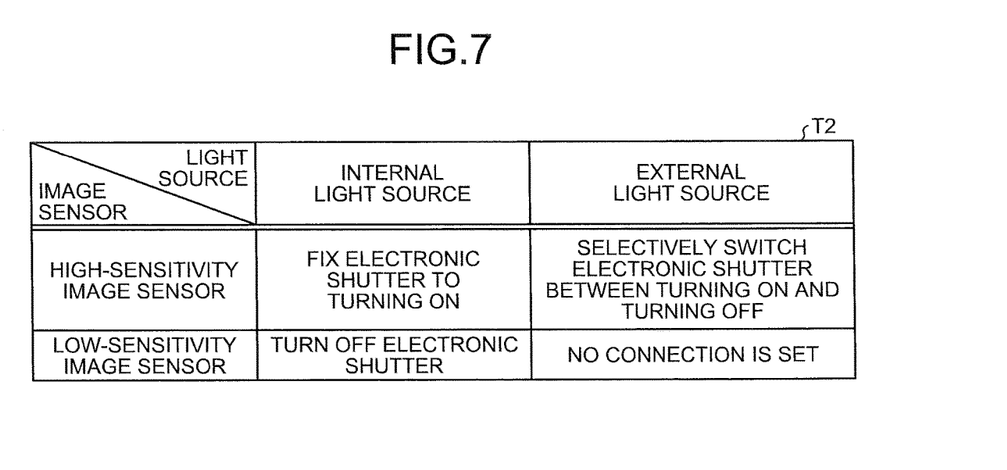
FIG. 7 is a diagram illustrating an exemplary control pattern table stored in a storage unit illustrated in FIG. 6.

A storage unit 36 stores a control pattern table 2361. FIG. 7 is a diagram illustrating an example of the control pattern table 2361 stored in the storage unit 36. As illustrated in FIG. 7, the storage unit 36 stores a table T2 as the control pattern table 2361, in which the control pattern of the electronic shutter function of the image sensor 22 is associated with each combination of the classification of the image sensor 22 and the classification of the light source. Here, a high-sensitivity image sensor (first image sensor) having sensitivity higher than predetermined reference sensitivity and a low-sensitivity image sensor (second image sensor) having sensitivity lower than the reference sensitivity serve as the image sensors 22. The light source identification unit 371 identifies which one of the high-sensitivity image sensor and the low-sensitivity image sensor is employed as the image sensor 22 used for observation. In table T2, a control pattern to fix the electronic shutter function to always turning on is associated with a combination of the internal light source and the high-sensitivity image sensor, whereas a control pattern to selectively switch the electronic shutter function between turning on and turning off is associated with a combination of the external light source and the high-sensitivity image sensor. In table T2, a control pattern to always turn off the electronic shutter function is associated with a combination of the internal light source and the low-sensitivity image sensor. Note that, regarding a combination of the external light source and the low-sensitivity image sensor, connection of such a combination is not actually set.

Figure 8:
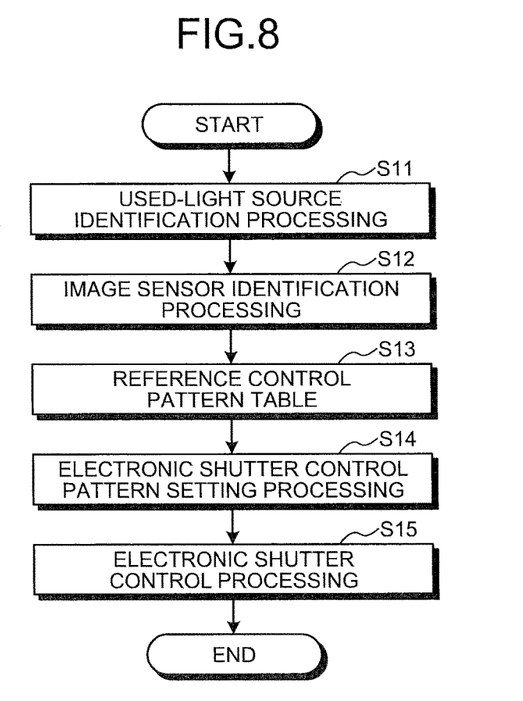
FIG. 8 is a flowchart illustrating processing procedures of electronic shutter function control processing for an image sensor of an endoscope by a light source integrated processor illustrated in FIG. 6.

FIG. 8 is a flowchart illustrating processing procedures of electronic shutter function control processing for the image sensor 22 of an endoscope 2 by the light source integrated processor 203. Step S11 illustrated in FIG. 8 corresponds to step S1 illustrated in FIG. 3. The endoscope identification unit 372 retrieves the identification information from a memory 24 of the endoscope 2 electrically mounted on the light source integrated processor 203, thereby carrying out image sensor identification processing to identify the classification of the image sensor 22 of the endoscope 2 (step S12). The electronic shutter control pattern setting unit 2374 references the control pattern table 2361 in the storage unit 36 (step S13) to retrieve, from the control pattern table 2361, the control pattern of the electronic shutter function according to the classification of the light source identified by the light source identification unit 371 and the classification of the image sensor 22 identified by the endoscope identification unit 372 and then carries out electronic shutter control pattern setting processing to set the retrieved control pattern as the control pattern of the electronic shutter function of the image sensor 22 (step S14). Step S15 illustrated in FIG. 8 corresponds to step S4 illustrated in FIG. 3.

When the light source identification unit 371 identifies, during the used-light source identification processing (step S11), that the light source used for observation is the internal light source (first light source 351) and also the endoscope identification unit 372 identifies, during the image sensor identification processing (step S12), that the classification of the image sensor 22 of the endoscope 2 mounted on the light source integrated processor 203 is the high-sensitivity image sensor, the electronic shutter control pattern setting unit 2374 references the table T2 (step S13) and then sets a control pattern to fix the electronic shutter function to always turning on (step S14). Accordingly, when the white light from the first light source 351 is used for observation, the electronic shutter controller 375 controls the image sensor 22 with high sensitivity using the control pattern to fix the electronic shutter function to always turning on and thus, the amount of exposure in the image sensor 22 is adjusted as appropriate in accordance with the brightness of an image.

When the light source identification unit 371 identifies, during the used-light source identification processing (step S11), that the light source used for observation is the external light source (second light source 52) and also the endoscope identification unit 372 identifies, during the image sensor identification processing (step S12), that the classification of the image sensor 22 is the high-sensitivity image sensor, the electronic shutter control pattern setting unit 2374 references the table T2 (step S13) and then sets a control pattern to selectively switch the electronic shutter function between turning on and turning off (step S14). Accordingly, when the infrared light from the second light source 52 is used for observation, the electronic shutter controller 375 selectively switches the electronic shutter function between turning on and off and thus, it is made possible to carry out control not to limit the exposure time through an electronic shutter such that sufficient brightness is ensured even with darker infrared light.

When the light source identification unit 371 identifies, during the used-light source identification processing (step S11), that the light source used for observation is the internal light source (first light source 351) and also the endoscope identification unit 372 identifies, during the image sensor identification processing (step S12), that the classification of the image sensor 22 is the low-sensitivity image sensor, the electronic shutter control pattern setting unit 2374 references the table T2 (step S13) and then sets a control pattern to always turn off the electronic shutter function (step S14). Accordingly, the electronic shutter controller 375 carries out control to always turn off the electronic shutter function and allow exposure during an entire period such that sufficient brightness is ensured even with the low-sensitivity image sensor. Note that, when the light source identification unit 371 identifies, during the used-light source identification processing (step S11), that the light source used for observation is the external light source (second light source 52) and also the endoscope identification unit 372 identifies, during the image sensor identification processing (step S12), that the classification of the image sensor 22 is the low-sensitivity image sensor, an error sound or the like is output to notify that connection other than the setting has been made, since such connection is not actually set.

As in this second embodiment, the control pattern of the electronic shutter function of the image sensor 22 is set in accordance with not only the classification of the light source used for observation but also the classification of the image sensor 22 of the endoscope 2 mounted on the light source integrated processor 203. Consequently, control of the electronic shutter function provided in the image sensor 22 can be further optimized.

Modified Example of Second Embodiment

Figure 9:
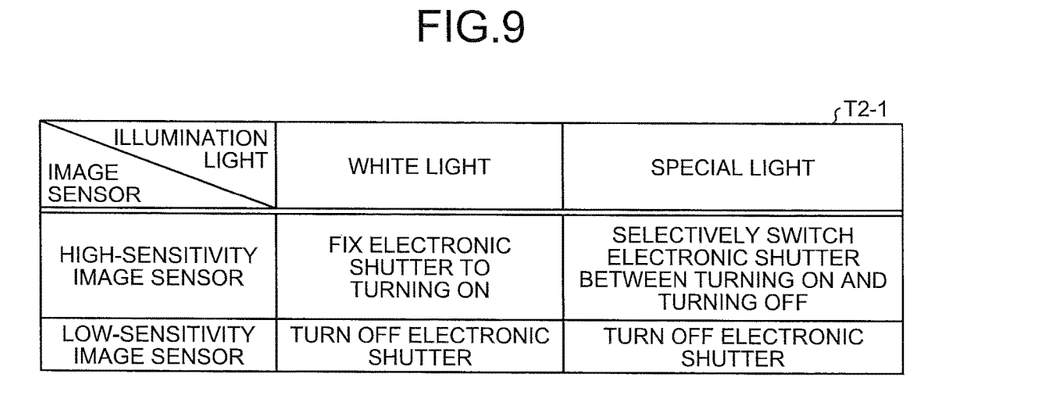
FIG. 9 is a diagram illustrating another exemplary control pattern table stored in a storage unit illustrated in FIG. 6.

FIG. 9 is a diagram illustrating another exemplary control pattern table 2361 stored in a storage unit 36. As illustrated in FIG. 9, the storage unit 36 may store a table T2-1 in which the control pattern of the electronic shutter function of an image sensor 22 is associated with each combination of the classification of illumination light and the classification of the image sensor 22. In this case, a light source identification unit 371 identifies, during the used-light source identification processing (step S11), which one of the white light and the special light is employed as the illumination light with which the subject is to be irradiated, based on the instruction information on observation light and the classification of the light source used for observation input from the input unit 38. The special light is, for example, red light or NBI light.

Specifically, when the light source identification unit 371 identifies, during the used-light source identification processing (step S11), that the illumination light is the white light and also an endoscope identification unit 372 identifies, during the image sensor identification processing (step S12), that the classification of the image sensor 22 is the high-sensitivity image sensor, an electronic shutter control pattern setting unit 2374 references the table T2-1 (step S13) and then sets a control pattern to fix the electronic shutter function to always turning on (step S14).

When the light source identification unit 371 identifies, during the used-light source identification processing (step S11), that the illumination light is the special light and also the endoscope identification unit 372 identifies, during the image sensor identification processing (step S12), that the classification of the image sensor 22 is the high-sensitivity image sensor, the electronic shutter control pattern setting unit 2374 references the table T2-1 (step S13) and then sets a control pattern to selectively switch the electronic shutter function between turning on and turning off (step S14), thereby ensuring sufficient brightness even with darker infrared light.

When the endoscope identification unit 372 identifies, during the image sensor identification processing (step S12), that the classification of the image sensor 22 is the low-sensitivity image sensor, the electronic shutter control pattern setting unit 2374 sets a control pattern to always turn off the electronic shutter function on the basis of the table T2-1 (step S14), regardless of which one of the white light and the special light is indicated by an identification result of the used-light source identification processing (step S11) by the light source identification unit 371, thereby ensuring sufficient brightness.

As in this modified example of the second embodiment, control of the electronic shutter function may be optimized using the control pattern according to the classification of the illumination light and the classification of the image sensor.

Figure 10:
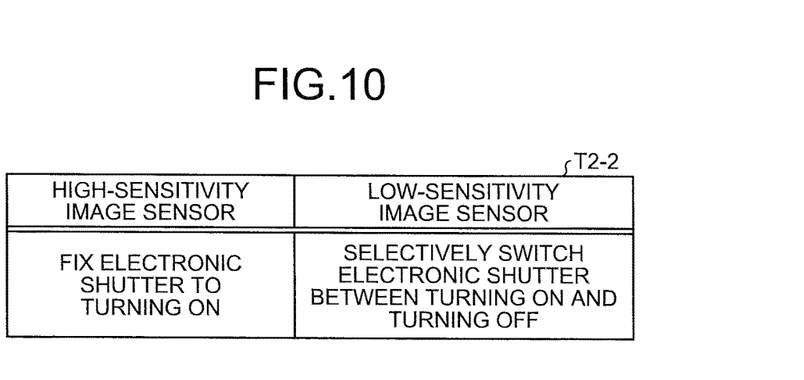
FIG. 10 is a diagram illustrating another exemplary control pattern table stored in a storage unit illustrated in FIG. 6.

As a matter of course, a light source integrated processor 203 may set the control pattern of the electronic shutter function of the image sensor 22 in accordance with the classification of the image sensor 22. FIG. 10 is a diagram illustrating another exemplary control pattern table 2361 stored in the storage unit 36. As illustrated in FIG. 10, the storage unit 36 may store a table T2-2 in which the control pattern of the electronic shutter function of the image sensor 22 is associated with the classification of the image sensor 22. In this case, when the endoscope identification unit 372 identifies that the classification of the image sensor 22 is the high-sensitivity image sensor, the electronic shutter control pattern setting unit 2374 simply sets a control pattern to fix the electronic shutter function to always turning on, based on the table T2-2 regardless of the classifications of the light source and the illumination light and, when the endoscope identification unit 372 identifies that the classification of the image sensor 22 is the low-sensitivity image sensor, sets a control pattern to selectively switch the electronic shutter function between turning on and turning off.

Additionally, although the embodiments have described the light source integrated processors 3, 3-1, and 203 in which light sources are integrated as examples, it is apparent that the embodiments can be similarly applied to a case where a processor and a light source device are provided as separate bodies.

Furthermore, a signal sent and received between the endoscope 2 and each of the light source integrated processors 3, 3-1, and 203 in the embodiments is not limited to an electrical signal but may be an optical signal obtained by converting the electrical signal. In this case, a transmission path for the optical signal such as an optical fiber is used to transmit the optical signal between the endoscope 2 and each of the light source integrated processors 3, 3-1, and 203. As a matter of course, wireless communication may be used in addition to wired communication to send and receive the signal between the endoscope 2 and each of the light source integrated processors 3, 3-1, and 203.

The embodiments have described the endoscope system utilizing the endoscope including the flexible insertion portion. However, as a matter of course, an endoscope system utilizing an endoscope including a hard insertion portion may be employed. In addition, the endoscope may be equipped with a light source and a control function for controlling the image sensor and the light source. In this case, the light source is not limited to a type where the light source is configured as a separate body from the endoscope but may be a semiconductor light source or the like provided at the distal end of the insertion portion of the endoscope. Meanwhile, the configuration is not limited to one in which the image sensor is provided at the distal end of the insertion portion of the endoscope. For example, the image sensor may be configured in such a manner as to be provided at a proximal end of the insertion portion such that an optical image transmitted from the distal end to the proximal end of the insertion portion through an optical fiber is captured. Furthermore, the endoscope is not limited to one including the image sensor provided at the distal end of the insertion portion but a configuration for connecting an eyepiece camera head of an optical endoscope such as a fiber scope or an optical viewing tube may be employed.

In addition, although the endoscope systems 1, 1-1, and 201 for medical use have been exemplified as the embodiments in the description, it is apparent that the embodiments also can be applied to an endoscope system for industrial use.

Furthermore, execution programs corresponding to the respective processing procedures carried out by the light source integrated processors 3, 3-1, and 203 according to the embodiments may be configured so as to be provided by being recorded in a recording medium readable by a computer, such as a CD-ROM, a flexible disk, a CD-R, and a DVD, as a file in an installable format or in an executable format, or alternatively, may be configured so as to be saved and kept in a computer connected to a network such as the Internet such that the provision thereof is by way of download via the network.

According to the invention, a classification of a light source emitting the illumination light is identified and an electronic shutter function of an image sensor is controlled based on a control pattern according to the identified classification of the light source. Consequently, an image with proper brightness can be obtained regardless of classifications of light sources.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
an imaging device including an image sensor provided with an electronic shutter function, the imaging device being configured to capture a subject;
a light source configured to emit illumination light for illuminating the subject;
an identification unit configured to identify which one of a first light source and a second light source configured to emit light having a wavelength bandwidth different from a wavelength bandwidth of the first light source is employed as the light source used for observation;
an electronic shutter controller configured to control the electronic shutter function of the image sensor based on a control pattern according to the classification of the light source identified by the identification unit; and
an electronic shutter control pattern setting unit configured to set a control pattern of the electronic shutter function in accordance with the classification of the light source identified by the identification unit,
wherein the electronic shutter control pattern setting unit sets a control pattern to use the electronic shutter function when the identification unit identifies that the light source is the first light source and sets a control pattern to selectively make switching between using the electronic shutter function and not using the electronic shutter function when the identification unit identifies that the light source is the second light source.

2. The imaging system according to claim 1, wherein the first light source is an internal light source provided within a same casing device as an imaging signal processing unit configured to process an imaging signal generated by the image sensor,
the second light source is provided at an external light source device configured as a separate body from the casing device, and
the identification unit identifies which one of the internal light source and the external light source device is employed as the light source used for observation.

3. The imaging system according to claim 2, wherein the external light source device emits light having an infrared wavelength bandwidth as the illumination light for the subject.

4. An imaging system comprising:
an imaging device including an image sensor provided with an electronic shutter function, the imaging device being configured to capture a subject;
a light source configured to emit illumination light for illuminating the subject;
an identification unit configured to identify a classification of a light source used for observation and a classification of the image sensor; and
an electric shutter controller configured to control the electronic shutter function of the image sensor based on a control pattern according to the classification of the light source and the classification of the image sensor identified by the identification unit.

5. The imaging system according to claim 4, further comprising an electronic shutter control pattern setting unit configured to set a control pattern of the electronic shutter function in accordance with the classification of the light source and the classification of the image sensor identified by the identification unit, wherein the electronic shutter controller controls the electronic shutter function of the image sensor based on the control pattern set by the electronic shutter control pattern setting unit.

6. The imaging system according to claim 5, wherein
the image sensor is a first image sensor having sensitivity higher than reference sensitivity or a second image sensor having sensitivity lower than the reference sensitivity,
the identification unit identifies which one of the first image sensor and the second image sensor is employed as the image sensor used for observation, and
the electronic shutter control pattern setting unit sets a control pattern to use the electronic shutter when the identification unit identifies that the image sensor is the first image sensor and sets a control pattern not to use the electronic shutter when the identification unit identifies that the image sensor is the second image sensor.

7. An imaging system comprising:
an imaging device including an image sensor provided with an electronic shutter function, the imaging device being configured to capture a subject;
a light source configured to emit illumination light for illuminating the subject;
an identification unit configured to identify a classification of a light source used for observation; and
an electronic shutter controller configured to control the electronic shutter function of the image sensor based on a control pattern according to the classification of the light source identified by the identification unit; and
a photometry unit configured to measure brightness of an object to be captured by the image sensor, wherein
the electronic shutter controller alters an exposure time of the image sensor based on the control pattern and a photometric value by the photometry unit.

8. The imaging system according to claim 5, wherein
the electronic shutter control pattern setting unit sets a control pattern of the electronic shutter function from among a control pattern to always turn off the electronic shutter function, a control pattern to always turn on the electronic shutter function, and a control pattern to selectively switch the electronic shutter function between turning on and turning off.

* * * * *